(12) United States Patent
Brown et al.

(10) Patent No.: US 8,242,041 B2
(45) Date of Patent: Aug. 14, 2012

(54) OXYGENATE CONVERSION CATALYST SYSTEM AND PROCESSES FOR MAKING AND USING SAME

(75) Inventors: Stephen H. Brown, Bernardsville, NJ (US); Guang Cao, Princeton, NJ (US); Teng Xu, Hampton, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 746 days.

(21) Appl. No.: 12/352,433

(22) Filed: Jan. 12, 2009

(65) Prior Publication Data

US 2010/0179363 A1 Jul. 15, 2010

(51) Int. Cl.
*B01J 29/03* (2006.01)
*B01J 31/00* (2006.01)

(52) U.S. Cl. ............... 502/60; 502/62; 502/63; 502/64; 502/208; 502/209; 502/210; 502/211; 502/213; 502/214; 502/150; 502/168; 502/172

(58) Field of Classification Search .................. 502/60, 502/62, 63, 64, 208, 209, 210, 211, 213, 502/214, 150, 167, 168, 172
See application file for complete search history.

(56) References Cited

U.S. PATENT DOCUMENTS

| | | | |
|---|---|---|---|
| 6,051,746 A * | 4/2000 | Sun et al. ...................... 585/639 |
| 6,441,262 B1 | 8/2002 | Fung et al. | |
| 6,444,868 B1 | 9/2002 | Vaughn et al. | |
| 6,482,999 B2 | 11/2002 | Fung et al. | |
| 6,518,475 B2 | 2/2003 | Fung et al. | |
| 6,657,022 B2 | 12/2003 | Williams et al. | |
| 6,734,330 B1 | 5/2004 | Xu et al. | |
| 6,743,747 B1 | 6/2004 | Xu et al. | |
| 6,844,476 B2 | 1/2005 | Vaughn et al. | |
| 7,045,672 B2 | 5/2006 | Xu et al. | |
| 7,057,083 B2 | 6/2006 | Xu et al. | |
| 7,084,319 B2 | 8/2006 | Kuechler et al. | |
| 7,132,581 B2 | 11/2006 | Xu et al. | |
| 7,199,277 B2 | 4/2007 | Xu et al. | |
| 2006/0135834 A1 | 6/2006 | Xu et al. | |

OTHER PUBLICATIONS

Song et al., "Supramoleclar Origins of Product Selectivity for Methanol-to Olefin Catalysis on HSAPO-34", J. Am. Chem. Sco., 2001, 123, pags. 4749-4754.*

* cited by examiner

*Primary Examiner* — Elizabeth Wood
(74) *Attorney, Agent, or Firm* — David M. Weisberg; Kevin M. Faulkner (57) ABSTRACT

The invention includes a method for impregnating a molecular sieve primary catalyst with an aromatic co-catalyst, the method comprising contacting the small pore molecular sieve primary catalyst having a porous framework structure with a combination of from at least 50 wt % to about 99.9 wt % of an aromatic co-catalyst and from about 0.1 wt % to less than 50 wt % of a polar impregnation agent containing one or more heteroatoms selected from the group consisting of nitrogen, oxygen, sulfur, phosphorus, and boron, under conditions sufficient to impregnate the porous framework structure of the primary catalyst with the aromatic co-catalyst (and optionally also with the polar impregnation agent), thus forming an integrated catalyst system. Methods for converting oxygenates to olefins using said integrated catalyst system are also described herein.

4 Claims, 5 Drawing Sheets

OXYGENATE CONVERSION CATALYST SYSTEM AND PROCESSES FOR MAKING AND USING SAME

FIELD OF THE INVENTION

The present invention relates to methods for impregnating molecular sieves with organic co-catalytic molecules, as well as integrated catalyst systems made by said methods and methods of converting oxygenates to olefins using said integrated catalyst systems.

BACKGROUND OF THE INVENTION

The use of molecular sieves as catalytic agents in hydrocarbon conversion processes is relatively well known. It has previously been suggested that, unlike in cracking-based (e.g., FCC) or dehydration-based (e.g. ETE) hydrocarbon conversion processes, molecular sieve catalysts in carbon-assembling processes (e.g., OTO/MTO) can benefit from organic material within the pore structure of the molecular sieve that can act as co-catalysts.

Coincidentally, there have been studies of oxygenates-to-olefins reaction systems (carbon-assembling processes) that indicate transformation of the oxygenate feedstock into organic material within the molecular sieve pore structure in an initial induction period. It has been suggested that the organic material formed within the molecular sieve during this initial induction period further catalytically enhances oxygenate conversion, e.g. into olefins, in OTO processes.

As a result, some publications have advocated pre-pooling, or pre-treating a molecular sieve catalyst with feedstock that reacts to form organic material similar to (if not identical to) the organic material formed during the initial induction period, in order to take advantage of the supposed further catalytic effect of such organic material within the already catalytic molecular sieve. Exemplary disclosures suggesting such molecular sieve pre-treatments include, but may not be limited to, U.S. Pat. Nos. 6,441,262, 6,444,868, 6,482,999, 6,518,475, 6,657,022, 6,734,330, 6,734,747, 6,844,476, 7,045,672, 7,057,083, 7,084,319, 7,132,581, and 7,199,277, as well as U.S. Patent Application Publication No. 2006/0135834 A1.

Nevertheless, such pre-treatments, by their reactive nature, tend to yield a wide distribution of organic materials within the molecular sieve pore structure. Indeed, due to the breadth of variety of the organic material formed during a pre-treatment, some portion of these organic materials may be non-catalytic or detrimental to the catalytic influence of the molecular sieve in the oxygenate conversion reactions they were intended to enhance.

Furthermore, particularly when relatively small pore molecular sieves (i.e., pore size of about 5 Å or less) are utilized as primary catalysts for MTO/OTO conversion reactions, the relatively small pore openings tend to limit the types of organic material precursors that can be used in the pre-treatment process.

SUMMARY OF THE INVENTION

However, it has now been unexpectedly discovered that certain single-ring aromatic and bulky unsaturated compounds can, under certain conditions, be impregnated within the pores/cages of relatively small pore molecular sieves, even in cases where previous attempts have failed due to the relatively large kinetic diameter of the compounds. This unexpected discovery has made it possible to select organic material that is the most catalytically active and to impregnate such organic material co-catalyst(s) within the relatively small pore structure of molecular sieve primary catalyst(s), and preferably to attain a relatively uniform distribution of such organic material co-catalyst(s) therewithin.

One aspect of the invention relates to an integrated catalyst system comprising a molecular sieve primary catalyst having a porous framework structure, within which is impregnated an aromatic co-catalyst (e.g., having a kinetic diameter equal to or up to 2.0 Angstroms larger than the pore diameter of the molecular sieve primary catalyst) and optionally a polar impregnation agent containing one or more heteroatoms selected from the group consisting of nitrogen, oxygen, sulfur, phosphorus, and boron, wherein the molecular sieve primary catalyst (i) has an 8-membered ring porous framework structure, (ii) has a porous framework structure that is defined by a pore size not greater than 5.0 Angstroms and that exhibits an AEI framework type, a CHA framework type, or both, or (iii) has both (i) and (ii).

Another aspect of the invention relates to a method for impregnating a molecular sieve primary catalyst with an aromatic co-catalyst, the method comprising contacting the small pore molecular sieve primary catalyst having a porous framework structure with a combination of from at least 50 wt % to about 99.9 wt % of an aromatic co-catalyst and from about 0.1 wt % to less than 50 wt % of a polar impregnation agent containing one or more heteroatoms selected from the group consisting of nitrogen, oxygen, sulfur, phosphorus, and boron, under conditions sufficient to impregnate the porous framework structure of the primary catalyst with the aromatic co-catalyst (and optionally also with the polar impregnation agent), thus forming an integrated catalyst system (such as described in the previous aspect of the invention), wherein the molecular sieve primary catalyst (i) has an 8-membered ring porous framework structure, (ii) has a porous framework structure that is defined by a pore size not greater than 5.0 Angstroms and that exhibits an AEI framework type, a CHA framework type, or both, or (iii) has both (i) and (ii).

Still another aspect of the invention relates to a method for converting an oxygenate feedstock into an olefin-containing product, the method comprising: impregnating a molecular sieve primary catalyst with an aromatic co-catalyst according to the method of the previous aspect of the invention in order to form an integrated catalyst system; contacting the oxygenate feedstock with the integrated catalyst system under conditions sufficient to form an olefin-containing product; and separating one or more olefins from the olefin-containing product. In a particularly advantageous embodiment of this aspect of the invention, the one or more olefins separated from the olefin-containing product can optionally but preferably be contacted with a polymer-forming catalyst, optionally also in the presence of one or more additional olefin monomers, under conditions sufficient to form an olefin-containing polymer, especially when the one or more olefins comprises ethylene and/or propylene.

There have been reports on a "ship-in-a-bottle" approach for entrapping molecules within a zeolitic structure in the literature. This approach, however, is different from one used in the present invention. Whereas the "ship-in-a-bottle" method exploits chemical reactions that result in the assembly of larger molecules from smaller ones within a zeolitic or zeolite-like cage, the methods of this invention involve insertion of "preassembled" molecules intact inside the cages without alteration to the molecules (indeed, by instead temporarily manipulating the porous framework structure of the molecular sieve). Thus, the methods of the present invention provide an unprecedented level of control over pre-pooling in molecular sieves.

BRIEF DESCRIPTION OF THE DRAWINGS

The present invention may be better understood by reference to the Detailed Description of the Preferred Embodiments, taken together with the attached Figures, wherein.

DETAILED DESCRIPTION OF THE PREFERRED EMBODIMENTS

The present invention provides a method for impregnating a molecular sieve primary catalyst with a bulky unsaturated or aromatic co-catalyst (abbreviated hereinafter as "aromatic co-catalyst"), the method comprising: contacting the molecular sieve primary catalyst having a porous framework structure with a combination of an aromatic co-catalyst and a polar impregnation agent containing one or more heteroatoms selected from the group consisting of nitrogen, oxygen, sulfur, phosphorus, and boron, under conditions sufficient to impregnate the porous framework structure of the primary catalyst with the aromatic co-catalyst, thus forming an integrated catalyst system.

As described herein, a "bulky" co-catalyst should be understood to mean one that has a kinetic diameter equal to or greater than (typically greater than) the pore diameter of the molecular sieve primary catalyst but equal to or less than (typically less than) the cage diameter of the molecular sieve primary catalyst, such that the co-catalyst, if capable of somehow entering a pore of the porous framework structure, would nevertheless be capable of being trapped within a cage of the porous framework structure of the molecular sieve primary catalyst.

In a preferred embodiment, the molecular sieve primary catalyst has (i) an 8-membered ring porous framework structure, (ii) a porous framework structure that is defined by a pore size not greater than 5.0 Angstroms and that exhibits an AEI framework type, a CHA framework type, or both, or (iii) both (i) and (ii). Examples of molecular sieve primary catalysts useful in such preferred embodiments can include, but are not limited to, small pore molecular sieves (i.e., those having a porous framework structure that is defined by a pore size not greater than 5.0 Angstroms) containing at least two of aluminum, silicon, and phosphorus within their framework structure (e.g. aluminosilicates, aluminophosphates, silicoaluminophosphates, silicophosphates, and the like, as well as metal-containing versions/derivatives thereof), including molecular sieves having less than 10-membered ring framework structures (for clarification, molecular sieves having hybrid 8/10-membered ring framework structures, so long as their pore diameter does not exceed 5.0 Angstroms, may be included). Other small pore molecular sieve framework types can include, but are not limited to, 8-membered ring framework structures (e.g. ABW, ACO, AEI, AEN, AFN, AFT, AFX, ANA, APC, APD, ATN, ATT, ATV, AWO, AWW, BIK, BRE, CAS, CHA, DDR, DFT, EAB, EDI, ERI, ESV, GIS, GOO, ITE, JBW, KFI, LEV, LTA, MER, MON, MTF, NSI, PAU, PHI, RHO, RTE, RTH, SAS, SAT, SAV, SIV, THO, TSC, VNI, YUG, and ZON framework types), 9-membered ring framework structures (e.g., —CHI, LOV, NAT, RSN, SBN, STT, and VSV framework types), and combinations and/or intergrowths thereof. Additionally or alternately, depending on the situation, certain anisotropic 10-membered ring framework structures may be considered "small pore" molecular sieves, even though one of the channel dimensions may be larger than 5.0 Angstroms, particularly where the "average" of two different channel dimensions is still not greater than 5.0 Angstroms. Examples of this latter class of molecular sieves can include, but is not limited to, DAC, EPI, EUO, FER, LAU, MTT, MWW, STI, WEI, and —WEN framework types. See, e.g., Ch. Baerlocher et al., *Atlas of Zeolite Framework Types,* 5th rev. ed., Elsevier, 2001, for a rather comprehensive list of molecular sieves, framework types, channel dimensions, ring frameworks, and the like.

In a particularly preferred embodiment, the molecular sieve primary catalyst is a SAPO having an 8-membered ring framework structure and contains both (more preferably is an intergrowth of) AEI and CHA framework types.

In general, silicoaluminophosphate molecular sieves comprise a molecular framework of corner-sharing silica, alumina, and phosphate tetrahedral units. This type of framework is effective in converting various oxygenates into olefin products.

Metal-substituted SAPOs, generally known as MeAPSOs or metal-containing silicoaluminophosphates, can be used. The metal, Me, can include one or more alkali metal ions (Group IA), alkaline earth metal ions (Group IIA), rare earth ions (Group IIIB, including the Lanthanide elements, scandium, or yttrium), and the additional transition metal ions of Groups IVB, VB, VIB, VIIB, VIIIB, and IB.

Preferably, the Me represents one or more elements such as Zn, Mg, M, Co, Ni, Ga, Fe, Ti, Zr, Ge, Sn, and Cr. These atoms can be inserted into the tetrahedral framework through a tetrahedral unit. The metal oxide tetrahedral unit can carry a net electric charge, depending on the valence state of the metal substituent. When the metal component has a valence state of +2, +3, +4, +5, or +6, the net electric charge can be between −2 and +3. Incorporation of the metal component is typically accomplished by adding a metal-containing component during synthesis of the silicoaluminophosphate molecular sieve. However, post-synthesis methods, such as ion exchange, incipient wetness, dry mixing, wet mixing, mechanical mixing, or a combination thereof, can also be used.

The silicoaluminophosphate molecular sieves can be synthesized by hydrothermal crystallization methods generally known in the art. See, for example, U.S. Pat. Nos. 4,440,871, 4,861,743, 5,096,684, and 5,126,308, the methods of making of which are fully incorporated herein by reference. A reaction mixture can be formed by mixing together reactive silicon, aluminum, and phosphorus components, along with at least one template. Generally, the mixture is sealed and heated, preferably under autogenous pressure, to a temperature of at least about 100° C., preferably from about 100° C. to about 250° C., until a crystalline product is formed. Formation of the crystalline product can take anywhere from hours to as much as weeks. In some cases, stirring or seeding with crystalline material can facilitate the formation of the desired crystalline product.

Typically, the silicoaluminophosphate molecular sieve product can be formed in solution. It can be recovered by standard means, however, such as centrifugation and/or filtration. The product can also be washed, recovered (e.g., by the same means), and dried.

The molecular sieve catalyst may be incorporated into a solid composition, preferably solid particles, in which the catalyst is present in an amount effective to promote the desired conversion reaction. The solid particles may include a catalytically effective amount of the catalyst and matrix material, optionally but preferably at least one of a filler material and a binder material, to provide a desired property or properties, e.g., desired catalyst dilution, mechanical strength, and the like, to the solid composition. Such matrix materials are often, to some extent, porous in nature and often have some nonselective catalytic activity to promote the formation of undesired products and may or may not be effective to promote the desired chemical conversion. Such matrix, e.g., filler and binder, materials can include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-aluminazirconias, and mixtures of these.

The solid particles can comprise from about 1% to about 99%, preferably from about 5% to about 90%, more preferably about 10% to about 80%, by weight of catalyst; and an amount from about 1% to about 99%, preferably from about 5% to about 90%, more preferably from about 10% to about 80%, by weight of matrix material.

The preparation of solid compositions, e.g. solid particles, comprising the catalyst and matrix material, is conventional and well known in the art and, therefore, is not discussed in detail here.

As a result of the crystallization process, the recovered molecular sieve typically contains within its pores/cages at least a portion of the template used in making the initial reaction mixture. The crystalline structure essentially wraps around the template, and the template must be removed to obtain catalytic activity. Once the template is removed, the crystalline structure that remains has what is typically called an intracrystalline pore system or a porous framework structure.

Molecular sieves can be made using and/or can contain one or more templates. Templates are structure directing agents, and typically contain nitrogen, phosphorus, oxygen, carbon, hydrogen, or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates can include tetraalkylammonium salts such as tetraethylammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine, and the like, and combinations thereof. Preferred templates can include triethylamine, cyclohexylamine, piperidine, pyridine, isopropylamine, tetraethylammonium salts, and mixtures thereof. The salts can include, but are not limited to, hydroxides (e.g., such as TEAOH), phosphates, fluorides, bromides, chlorides, acetates, and the like. Preferred tetraalkylammonium salts include the hydroxide and phosphate forms.

As is known in the art, a templated molecular sieve (or catalyst composition containing the molecular sieve) must be activated prior to use in a catalytic process. As used herein the activation of a templated molecular sieve (catalyst composition) means that the template(s) is(are) removed from the porous framework structure, leaving active catalytic sites open for catalyzing feed conversion. This type of activation process can be accomplished by calcining, or essentially heating the template(s), at a temperature from about 200° C. to about 800° C., typically in the presence of an oxygen-containing gas. In some cases, it may be desirable to heat in an environment having a low concentration of oxidizing agent (e.g. oxygen gas). This type of process can be used for partial or complete removal of the template from the intracrystalline pore system. In other cases, particularly with smaller templates, complete or partial removal from the sieve can be accomplished by conventional desorption processes, such as those used in making standard zeolites.

Once the template has been removed from the molecular sieve (catalyst composition), the molecular sieve can be impregnated with the aromatic co-catalyst in an impregnation zone to form an integrated catalyst system. Once the co-catalyst is impregnated within the porous framework structure of the molecular sieve primary catalyst, the integrated catalyst system can be allowed to stand for some time without contacting the feedstock. It is preferable, however, to maintain the integrated catalyst system in a relatively inert environment, particularly if there is to be an extended time before the integrated catalyst system is contacted with the oxygenate feed.

Typically, the co-catalyst according to the invention will have a kinetic diameter equal to, or up to about 2.0 Angstroms greater than (e.g., equal to or up to about 1.5 Angstroms greater than), the pore diameter of the molecular sieve primary catalyst. When a preferred molecular sieve primary catalyst is being used, exemplary co-catalysts can include, but are not limited to, single-ring aromatic compounds having one or more hydrocarbon substitution, $C_5$-$C_{14}$ linear, branched, or cyclic non-aromatic hydrocarbons having at least one unit of unsaturation, and combinations thereof.

Single-ring aromatic compounds, for example, are believed to have higher co-catalytic value, when combined with certain molecular sieve primary catalysts, in OTO/MTO conversion reactions, than multi-ring aromatic compounds and/or fully saturated hydrocarbon compounds. Importantly, virtually all single-ring aromatic structures have atomic sizes larger than the pore openings of certain molecular sieves (e.g., CHA framework-type molecular sieves, AEI framework-type molecular sieves, or combinations or intergrowths thereof), a fact which has frustrated previous attempts to impregnate such molecular sieves with such organic material and had previously led to the aforementioned pre-treatment options.

Exemplary single-ring aromatic compounds can include, but are not limited to, benzene, toluene, a xylene, ethylbenzene, a methylethylbenzene, a trimethylbenzene, a diethylbenzene, a cyclopentadienyl moiety, pyridine, a methylpyridine, an ethylpyridine, a dimethylpyridine, a methylethylpyridine, a trimethylpyridine, a diethylpyridine, and the like, and combinations thereof. When a pyridine compound is used as the single ring aromatic compound, depending upon the molecular sieve primary catalyst and the impregnation conditions, a polar impregnation may not be necessary (or, to explain further, the pyridine compound may act as its own polar impregnation agent due to the lone pair on the nitrogen in the pyridine ring).

Exemplary $C_5$-$C_{14}$ non-aromatic hydrocarbons can include, but are not limited to, cyclopentene, a $C_1$-$C_4$ singly-, doubly-, or triply-substituted cyclopentene, cyclopentadiene, a $C_1$-$C_4$ singly-, doubly-, triply-, or quadruply-substituted cyclopentadiene, a $C_1$-$C_4$ singly- or doubly-substituted cyclobutene, a $C_1$-$C_4$ singly-, doubly-, or triply-substituted butene, a $C_1$-$C_4$ singly- or doubly-substituted butadiene, a $C_1$-$C_4$ singly-, doubly-, triply-, or quadruply-substituted pentene, a $C_1$-$C_4$ singly-, doubly-, or triply-substituted pentadiene, cyclohexene, a $C_1$-$C_4$ singly-, doubly-, or triply-substituted cyclohexene, cyclohexadiene, a $C_1$-$C_4$ singly- or doubly-substituted cyclohexadiene, and the like, and combinations thereof.

The polar impregnation agent according to the invention can be inorganic or organic. Exemplary inorganic polar impregnation agents can include, but are not limited to, water (vapor), ammonia, hydrogen sulfide, hydroxylamine, phosphine, a hydrogen phosphate, phosphoric acid, boron trihydride, trihydroxyborane, a hydrogen borate, boric acid, and the like, and combinations thereof. Exemplary organic polar impregnation agents can include, but are not limited to, a $C_1$-$C_5$ alcohol such a methanol, ethanol, n-propanol, isopropanol, and the like; a $C_1$-$C_5$ diol such as ethylene glycol, propylene glycol, and the like; an amine compound $NR_3$, where each R group is independently hydrogen or a $C_1$-$C_5$ hydrocarbon, e.g., methylamine, ethylamine, propylamine, butylamine, dimethylamine, diethylamine, methylethylamine, diisopropylamine, trimethylamine, triethylamine, methyldiethylamine, methyldiisopropylamine, ethyldiisopropylamine, and the like; a hydroxy-amino-compound $R_2N$—$R'$—$OH$, where each R group is independently hydrogen or a $C_1$-$C_5$ hydrocarbon, and $R'$ is a $C_1$-$C_5$ hydrocarbon, e.g., alkanolamines such as ethanolamine, n-methylethanolamine, n,n-dimethylethanolamine, propanolamine, and the like; a thio-amino-compound $R_2N$—$R'$—$SH$, where each R group is independently hydrogen or a $C_1$-$C_5$ hydrocarbon, and $R'$ is a $C_1$-$C_5$ hydrocarbon; a hydroxy-thio-compound $RS$—$R'$—$OH$, where each R group is independently hydrogen or a $C_1$-$C_5$ hydrocarbon, and $R'$ is a $C_1$-$C_5$ hydrocarbon; an organic boron compound $BR_3$, where each R group is independently hydrogen or a $C_1$-$C_5$ hydrocarbon; mixtures thereof; and reaction products thereof, with themselves, each other, with an oxygen-containing gas, or with an inorganic polar impregnation agent.

Without being bound by theory, it is believed that the polar impregnation agent can react reversibly with the porous framework structure of the molecular sieve primary catalyst by reversibly breaking a framework bond (e.g., in a SAPO molecular sieve, this could be an Al—O—P or Si—O—P bond, for instance, in the pore window to a cage), thus creating a temporarily larger opening than normal. In this manner, it is believed that the aromatic co-catalyst, normally having too large a kinetic diameter to allow diffusion through the pores of the molecular sieve, can then diffuse through the temporarily larger pore opening into the cage. The reverse reaction can then heal the break, thereby trapping the aromatic co-catalyst within the cage.

Because the aromatic co-catalyst typically will have a higher activity in co-catalyzing a carbon-assembling hydrocarbon conversion reaction, it is typically desirable to load a higher proportion of aromatic co-catalyst within the porous framework structure of the primary catalyst than of the polar impregnation agent. Generally, the polar impregnation agent is present in the combination mostly to facilitate impregnation of the aromatic co-catalyst and usually not to act as a co-catalyst. For that reason, the combination to be contacted with the molecular sieve primary catalyst according to the methods of the invention typically contains predominantly the aromatic co-catalyst (i.e., at least 50% by weight of the combination) and typically contains a smaller amount (i.e., less than 50% by weight of the combination, or at least less than the co-catalyst, if there are additional combination components) of the polar impregnation agent.

In a preferred embodiment, therefore, the combination comprises from at least 50 wt % to about 99.9 wt % of the aromatic co-catalyst and from about 0.1 wt % to less than 50 wt % of the polar impregnation agent. In other preferred embodiments, the combination can comprise from about 60 wt % to about 99.9 wt %, from about 70 wt % to about 99.9 wt %, from about 80 wt % to about 99.9 wt %, from about 85 wt % to about 99.9 wt %, from about 85 wt % to about 99.5 wt %, from about 90 wt % to about 99.9 wt %, from about 90 wt % to about 99.5 wt %, from about 85 wt % to about 99 wt %, or from about 90 wt % to about 99 wt %, of the aromatic co-catalyst, based on the weight of the combination components contacting the molecular sieve primary catalyst under the impregnation conditions. In such preferred embodiments, the combination can also comprise from about 0.1 wt % to about 40 wt %, from about 0.1 wt % to about 30 wt %, from about 0.1 wt % to about 20 wt %, from about 0.1 wt % to about 15 wt %, from about 0.5 wt % to about 15 wt %, from about 0.1 wt % to about 10 wt %, from about 0.5 wt % to about 10 wt %, from about 1 wt % to about 15 wt %, or from about 1 wt % to about 10 wt %, of the polar impregnation agent, based on the weight of the combination components contacting the molecular sieve primary catalyst under the impregnation conditions.

In one embodiment, the conditions sufficient to impregnate the porous framework structure of the primary catalyst with the aromatic co-catalyst can include, but are not limited to a temperature from about 100° C. to about 500° C. (e.g., from about 200° C. to about 450° C.), a pressure of at least about 100 psig (e.g., from about 250 psig to about 3000 psig), and an exposure time of at least about 3 minutes. In a preferred embodiment, the impregnation temperature can be from about 225° C. to about 425° C., from about 250° C. to about 400° C., or from about 260° C. to about 380° C. In another preferred embodiment, the impregnation pressure can be from about 400 psig to about 2500 psig, from about 500 psig to about 2000 psig, from about 500 psig to about 1700 psig, from about 500 psig to about 1500 psig, from about 500 psig to about 1300 psig, from about 600 psig to about 2000 psig, from about 600 psig to about 1700 psig, from about 600 psig to about 1500 psig, from about 600 psig to about 1300 psig, from about 700 psig to about 2000 psig, from about 700 psig to about 1700 psig, from about 700 psig to about 1500 psig, from about 700 psig to about 1300 psig, from about 800 psig to about 2000 psig, from about 800 psig to about 1700 psig, from about 800 psig to about 1500 psig, from about 800 psig to about 1300 psig, or from about 800 psig to about 1200 psig. In yet another preferred embodiment, the impregnation time can be at least about 5 minutes, at least about 10 minutes, at least about 15 minutes, at least about 30 minutes, at least about 45 minutes, at least about 1 hour, at least about 2 hours, at least about 4 hours, at least about 8 hours, at least about 12 hours, at least about 16 hours, or at least about 24 hours. Nevertheless, as a reduction in overall impregnation time is desired, so long as sufficient co-catalyst impregnation is achieved, it may be advantageous to limit the impregnation time, for instance, to no more than 200 hours, no more than 150 hours, no more than 100 hours, no more than 75 hours, no more than 50 hours, no more than 25 hours, no more than 16 hours, no more than 12 hours, no more than 8 hours, no more than 4 hours, no more than 2 hours, no more than 1 hour, no more than 45 minutes, no more than 30 minutes, no more than 15 minutes, or no more than 10 minutes.

In an alternate embodiment, depending upon circumstances including the nature of both the molecular sieve and the co-catalyst (e.g. for certain SAPOs with certain pyridine-based co-catalyst compounds), the impregnation pressure may be lower than about 100 psig, e.g., as low as about 1 psig or 2 psig.

Of course, the impregnation time may be significantly impacted by the combination feed rate, which may be constant or may be varied during the impregnation time to achieve improved or optimal co-catalyst loading within the porous framework structure. Alternatively, the catalyst may be impregnated in a batch reactor, in which case the impregnation time may be significantly impacted by the order of addition of the ingredients, the temperature of the ingredients when they are added, and the rate of heating and cooling of the batch reactor. Without wishing to be bound, in a flow through system, the combination feed can have a weight hourly space velocity (WHSV) from about 0.01 $hr^{-1}$ to about 500 $hr^{-1}$, e.g., from about 0.1 $hr^{-1}$ to about 100 $hr^{-1}$, from about 1 $hr^{-1}$ to about 10 $hr^{-1}$, from about 1 $hr^{-1}$ to about 5 $hr^{-1}$, or the like.

In any event, the impregnation conditions can desirably result in a detectable proportion of the pores/cages of the porous framework structure of the primary catalyst containing a co-catalyst molecule. In a preferred embodiment, at least 10%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, and up to about 100% of the pores/cages of the porous framework structure of the primary catalyst can contain an aromatic co-catalyst and/or a polar impregnation agent (preferably at least or solely an aromatic co-catalyst) after impregnation. Evaluation of the integrated catalyst system to determine the extent of combination/co-catalyst loading within the porous framework structure of the molecular sieve primary catalyst can be accomplished with thermally programmed oxidation (TPO) analysis, carbon nuclear magnetic resonance (e.g. solid state $^{13}C$ NMR) analysis, or both.

In one embodiment, at least a portion of the polar impregnation agent can be removed from the porous framework structure after impregnation by further thermally treating the integrated catalyst system. In certain such embodiments, the thermal treatment can be conducted at a treatment temperature higher than the temperature sufficient to impregnate the porous framework structure, e.g., from about 275° C. to about 550° C. or from about 300° C. to about 500° C. Without wishing to be bound, the treatment time should be sufficient to sufficiently degrade the polar impregnation agent so as to allow degraded portions thereof to exit the porous framework structure of the molecular sieve. In one embodiment, the thermal treatment time can be at least about 5 minutes, preferably at least about 10 minutes, and can end at any time when the polar impregnation agent is either completely or desirably sufficiently removed (e.g., not longer than 24 hours).

Regardless of the composition of the combination prior to or during impregnation, the composition within the porous framework structure of the molecular sieve primary catalyst after impregnation and/or after any thermal treatment, if conducted, can advantageously be at least about 50 wt %, at least about 60 wt %, at least about 70 wt %, at least about 80 wt %, at least about 85 wt %, at least about 90 wt %, at least about 95 wt %, at least about 98 wt %, at least about 99 wt %, at least about 99.5 wt %, at least about 99.9 wt %, or as much as about 100 wt % of the aromatic co-catalyst, based on the weight of the combination components contacting the molecular sieve primary catalyst. As a result, the composition within the porous framework structure of the molecular sieve primary catalyst can advantageously be less than about 50 wt %, less than about 40 wt %, less than about 30 wt %, less than about 20 wt %, less than about 15 wt %, less than about 10 wt %, less than about 5 wt %, less than about 2 wt %, less than about 1.0 wt %, less than about 0.5 wt %, less than about 0.1 wt %, or substantially free from (meaning undetectably present) the polar impregnation agent, based on the weight of the combination components contacting the molecular sieve primary catalyst.

The present invention additionally includes integrated catalyst systems made according to the impregnation methods disclosed herein and comprising a molecular sieve primary catalyst having a porous framework structure, within which is impregnated the aromatic co-catalyst and optionally also the polar impregnation agent disclosed herein.

Furthermore, the present invention also includes using the integrated catalyst systems according to the invention in a method for converting an oxygenate feedstock into an olefin-containing product. In its most basic form, the method comprises: impregnating a molecular sieve primary catalyst with an aromatic co-catalyst according to the methods described herein to form an integrated catalyst system, or, if an impregnated catalyst system is already available, merely contacting the oxygenate feedstock with the integrated catalyst system under conditions sufficient to form an olefin-containing product, and then preferably separating one or more olefins from the olefin-containing product.

When the co-catalyst is aromatic, and not merely an unsaturated non-aromatic compound, the composition can be identified by a carbon NMR spectrum comprising a peak in the 18-40 ppm region and a peak in the 120-150 ppm region. In one embodiment, the aromatic co-catalyst comprises an alkyl-substituted single-ring aromatic compound. Alternatively, if the intensity of the peak in the 18-40 ppm region is negligible, a single peak near 128 ppm can indicate benzene, which is another useful co-catalyst. When a single-ring aromatic compound other than benzene is used as the co-catalyst, the ratio of the intensity of the peak in the 18-40 ppm region to the intensity of the peak in the 120-150 ppm region can advantageously be not greater than 1.0, for instance between about 0.15 and about 0.7.

It can be desirable that the aromatic co-catalyst be present within the porous framework structure of the molecular sieve primary catalyst in an amount effective to enhance the conversion of oxygenate feed to olefin product, particularly at a concentration effective to enhance selectivity to ethylene and/or propylene.

In a particularly preferred embodiment, the activity of an impregnated molecular sieve/co-catalyst system for oxygenate conversion can be increased by a factor of at least about 20% over an untreated, but otherwise identical molecular sieve primary catalyst. The selectivity to ethylene and/or propylene of such an integrated catalyst system in OTO (MTO) conversion reactions can be expected to increase by at least about 2 wt %, preferably at least about 3 wt %, at least about 4 wt %, or at least about 5 wt %, over an untreated catalyst.

The impregnation of the primary catalyst with the co-catalyst can occur in an impregnation zone, which preferably can be contained in a separate impregnation vessel or alternately within a reactor vessel where the oxygenate conversion reaction takes place. The impregnation vessel can be an auxiliary reactor associated (i.e., in at least intermittent fluid communication) with the oxygenate conversion reactor and regenerator system. The auxiliary reactor should generally be capable of continuously or intermittently receiving catalyst from the regenerator and of subsequently continuously or intermittently supplying impregnated catalyst/co-catalyst system to the oxygenate conversion reactor.

When impregnation is carried out within the same vessel where the catalytic conversion of oxygenate to olefin takes place, two separate temperature zones may be maintained to reflect the temperatures used in both the oxygenate conversion zone and the impregnation zone. Different conditions in the two zones may be maintained through control of the conditions at which the catalyst and feeds are introduced, including temperature, pressure, and/or phase. Optionally, each zone may comprise heating or cooling functions, e.g., such as steam or cooling water coils.

After impregnation, the integrated catalyst system comprising the molecular sieve primary catalyst and the co-catalyst within the porous framework structure thereof can be contacted with feed containing an oxygenate, and optionally a diluent or a co-feed, at process conditions effective to produce an olefin-containing product. The OTO reaction is carried out in an oxygenate reaction zone, and the reaction zone is contained within a catalytic reactor.

The oxygenate feedstock can comprise at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst system. When the oxygenate is an alcohol, the alcohol can include an aliphatic moiety having from 1 to 10 carbon atoms, more preferably from 1 to 4 carbon atoms. Representative alcohols include, but are not necessarily limited to, lower straight and branched chain aliphatic alcohols, their unsaturated counterparts, and their nitrogen, halogen, and sulfur analogs. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether, formaldehyde; dimethyl carbonate; dimethyl ketone; acetic acid; and the like; and mixtures thereof. Preferred oxygenate compounds include methanol, dimethyl ether, and mixtures thereof.

The method of making the olefin-containing product in this invention can include the process of making these compositions from hydrocarbons such as oil, coal, tar sands, shale, biomass, and natural gas, inter alia. Methods for making the compositions are known in the art. These methods can include, but are not limited to, fermentation to alcohol or ether, making synthesis gas, then converting the synthesis gas to alcohol or ether. Synthesis gas can be produced by known processes such as steam reforming, autothermal reforming, and partial oxidization.

One or more inert diluents may optionally be added with the feedstock, for example, in an amount of from 1 to 99 molar percent, based on the total number of moles of all feed and diluent components fed to the reaction zone. For purposes of this invention, diluents are relatively inert compositions that do not substantially participate in the oxygenate conversion reaction, i.e., they are neither created nor consumed and preferably do not substantially affect the oxygenate conversion reaction. Typical diluents include helium, argon, nitrogen, carbon monoxide, carbon dioxide, water, and mixtures thereof. When desired, preferred diluents include water and nitrogen. Water can be used in either liquid or vapor form.

Hydrocarbons other than oxygenates can optionally be included as part of the feedstock, i.e., as co-feed. These hydrocarbons can include olefins, paraffins, alkylaromatics, aromatics, or mixtures thereof. When desired, preferred hydrocarbon co-feeds can include, butylene, pentylene, $C_4^+$ hydrocarbons, $C_5^+$ hydrocarbons, and mixtures thereof. In this embodiment, particularly preferred are $C_4^+$ hydrocarbons, especially those obtained from separation and recycle of reactor product.

Typically, the oxygenate feed can be contacted with the integrated catalyst system when the oxygenate feed is in a vapor phase. Alternately, the process may be carried out with the feed in a liquid or a mixed vapor/liquid phase. When the process is carried out in a liquid phase or a mixed vapor/liquid phase, different conversions and selectivities of feed-to-product may result, depending upon the catalyst and reaction conditions.

Olefins can generally be produced at a wide range of temperatures. An effective operating temperature range for converting oxygenates to olefins can be from about 200° C. to about 700° C. At the lower end of the temperature range, the formation of the desired olefin products may become markedly low and/or slow. At the upper end of the temperature range, the process may not form an optimum amount of (desired olefin) product. Preferably, the oxygenate conversion process can be carried out at a temperature range between about 350° C. and about 600° C., more preferably between about 400° C. and about 550° C.

Examples of reactors which can be used in this invention include fluid bed reactors and concurrent riser reactors as described in "Free Fall Reactor," *Fluidization Engineering*, D. Kunii and O. Levenspiel, Robert E. Krieger Publishing Co. NY, 1977, expressly incorporated herein by reference. Additionally, countercurrent free fall reactors may be used in the conversion process, as described in U.S. Pat. No. 4,068,136 and in "Riser Reactor," *Fluidization and Fluid-Particle Systems*, pages 48-59, F. A. Zenz and D. F. Othmo, Reinhold Publishing Corp., NY 1960, the detailed descriptions of which are also expressly incorporated herein by reference.

When the oxygenate conversion reactor is a fluidized bed reactor, it is preferred that the reactor have at least a riser region and optionally also a dense fluid bed section. In the embodiment where a dense fluid bed section is present, the regenerated catalyst can be returned to the portion of the reactor above the dense phase region, immediately below the dense phase region, or anywhere between about the top one fourth of the riser region and the bottom one fourth of the dense phase region.

The oxygenate conversion reaction can take place at a weight hourly space velocity (WHSV) of from 1 $hr^{-1}$ to 1000 $hr^{-1}$. According to this invention, WHSV is defined as the weight of oxygenate, and any hydrocarbon which may be optionally added with the feed, per hour per weight of the molecular sieve content of the integrated catalyst system. Preferred reactors are co-current riser reactors and short contact time countercurrent free-fall reactors in which an oxygenate feedstock can be contacted with a molecular sieve catalyst at a WHSV of at least about 20 $hr^{-1}$, preferably from about 20 $hr^{-1}$ to about 500 $hr^{-1}$, and most preferably from about 20 $hr^{-1}$ to 250 $hr^{-1}$. Because the catalyst system or the feedstock may contain other materials which act as inerts or diluents, the WHSV is calculated on the weight basis of the oxygenate feed, and any hydrocarbon which may be present, and the molecular sieve contained in the catalyst system.

Effective pressures for the oxygenate conversion process can range from about 0.1 psia to about 500 psia. Preferred pressures can be from about 10 psia to about 250 psia, with particularly preferred pressures being from about 15 psia to about 200 psia. The foregoing pressures are inclusive of any inert diluent or additional hydrocarbon component, as well as the oxygenate compounds and/or mixtures thereof with hydrocarbon.

The level of conversion of the oxygenate feed, particularly during a steady state of the reaction, can be maintained at a sufficiently high level, e.g., to reduce the level of unwanted by-products and/or to avoid the need for commercially unacceptable levels of recycling of unreacted feeds. A reduction in unwanted by-products can be seen when conversion moves from roughly 100 mol % to about 98 mol % or less. Recycling up to as much as about 50 mol % of the feedstock can be commercially acceptable. Thus, conversions levels achieving both goals can range from about 50 mol % to about 98 mol % or desirably from about 85 mol % to about 98 mol %. However, it can be alternately acceptable to achieve conversion between 98 mol % and 100 mol %, in order to simplify the recycling process. Oxygenate conversion may be maintained at this level using a number of methods familiar to persons of ordinary skill in the art, such as adjusting reaction temperature, pressure, flow rate (i.e., space velocity), level/degree of catalyst regeneration, amount of catalyst re-circulation, specific reactor configuration, feed composition, and/or other parameters that can affect oxygenate conversion.

The residence time of the feed in the reaction zone may vary from fractions of a second to a number of hours, determined largely by the reaction temperature, the pressure, the molecular sieve catalyst selected, the WHSV, the phase (liquid or vapor), and the process design characteristics.

In the process of this invention, all or part of the catalyst typically suffers deactivation as a result of carbonaceous deposits forming on the catalyst during the olefin conversion reaction. The catalyst, therefore, should generally be periodically regenerated by contacting it with a regeneration medium to remove all or part of such deactivating carbonaceous deposits. This regeneration advantageously occurs in a regenerator separate from, but in fluid communication with, the oxygenate conversion reactor. Less advantageously (though still possibly), regeneration may occur periodically within the oxygenate conversion reactor by ceasing the flow of feed to the reactor, introducing a regeneration medium, ceasing flow of the regeneration medium, and then reintroducing the feed to the fully or partially regenerated catalyst. Regeneration preferably occurs periodically or continuously outside the reactor by removing a portion of the deactivated catalyst (e.g., preferably less than 50% by weight of the entire inventory of catalyst within the reaction system, such as less than 25% by weight) to a separate regenerator, and subsequently reintroducing the regenerated catalyst to the oxygenate conversion reactor. This is different from a typical Fluid Catalytic Cracker (FCC) riser reactor, where all or most of the catalyst exiting the reactor (e.g., and entering the disengaging zone) is sent to the regenerator. Periodic regeneration may occur at times and conditions needed to maintain a desired level of activity of the entire catalyst within the reactor.

According to one of the preferred embodiments of this invention, the catalyst containing carbonaceous material is regenerated under conditions effective to obtain a regenerated catalyst having a carbonaceous content of less than 2 wt %, preferably less than 1.5 wt % or less than 1.0 wt %, preferably based on the weight of the molecular sieve catalyst, but optionally based on the weight of the formulated molecular sieve catalyst, which includes any binder and/or matrix material. Following regeneration, the catalyst can preferably be sent to the impregnation zone to re-introduce the co-catalyst within the porous framework of the molecular sieve primary catalyst, before being returned to the oxygenate conversion reactor.

In order to make up for any catalyst loss during the regeneration or reaction processes, additional (fresh) catalyst can be added to the reaction system. Preferably, the fresh catalyst can be added to the regenerated catalyst after it is removed from the regenerator, but before the impregnation zone, so that both regenerated and fresh catalyst can be transformed into integrated catalyst systems containing the co-catalyst. However, in an alternate embodiment, the fresh catalyst can be impregnated independently of and/or separately from the regenerated catalyst, or, less preferably, added directly to the oxygenate conversion zone without impregnation.

In a preferred embodiment of the continuous operation, only a portion of the catalyst is removed from the reactor and sent to the regenerator to remove the accumulated carbonaceous deposits that result during the catalytic reaction. In the regenerator, the catalyst is advantageously contacted with a regeneration medium containing oxygen or other oxidants. Examples of oxidants, other than $O_2$, can include, but are not limited to, $O_3$, $SO_3$, $N_2O$ NO, $NO_2$, $N_2O_5$, and mixtures thereof It is preferred to supply $O_2$ in the form of air, although the oxygen content of the air can be reduced or increased by standard methods, as desired. The air can optionally be diluted with nitrogen, $CO_2$, or flue gas, and steam may be added. Desirably, the $O_2$ concentration in the regenerator can be reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, much of the deactivating carbonaceous deposits are removed from the catalyst during the regeneration process, forming a regenerated catalyst. The regenerated catalyst can then be sent to the impregnation zone for introducing the aromatic co-catalyst into the molecular sieve porous framework structure, although some of the regenerated catalyst can be sent directly to the reaction zone for catalytic contact with the feed. Typical regeneration temperatures can be from about 350° C. to about 800° C., desirably from about 400° C. to about 750° C. Preferably, regeneration can be carried out at a temperature from about 450° C. to about 700° C. Desirably, the catalyst regenerator can include a catalyst separator, such as a plurality of cyclones, to separate flue gases from the catalyst.

It may be desirable to strip at least some of the volatile organic components which may be adsorbed onto the catalyst or located within its porous framework structure prior to entering the regenerator. This can be accomplished by passing a stripping gas over the catalyst in a stripper or stripping chamber, which can be located within the reactor vessel or in a separate vessel. The stripping gas can be any substantially inert medium that is commonly used. Examples of stripping gas include, but are not limited to, steam, nitrogen, helium, argon, methane, $CO_2$, CO, flue gas, and mixtures thereof.

Additionally or alternatively, it may be desirable to cool at least a portion of the regenerated catalyst to a lower temperature, before it is sent to the impregnation zone and/or to the reaction zone. In one embodiment, a heat exchanger located externally to the regenerator may be used to remove some heat from the catalyst after it has been withdrawn from the regenerator. When the regenerated catalyst is cooled, it is desirable to cool it to a temperature from about 200° C. higher to about 200° C. lower than the temperature of the catalyst withdrawn from the reactor, more desirably from about 10° C. to about 200° C. lower. This cooled catalyst then may be sent to the impregnation zone or the reaction zone, or it may be recycled back to the regenerator. Introducing the cooled catalyst into the impregnation zone, the reaction zone, or the regenerator can serve to reduce the average temperature in the impregnation zone, reaction zone, or regenerator, as needed.

In a preferred embodiment of the invention, an average gas superficial velocity of greater than about 1 meter per second (m/s) is maintained in the oxygenate conversion zone, preferably greater than about 2 m/s, for example from about 2 m/s to about 40 m/s. As defined herein, gas superficial velocity (GSV) is the volumetric flow rate of the feedstock (including oxygenate, hydrocarbon, and any diluent) divided by the cross-sectional area of oxygenate conversion (reaction) zone. Since oxygenate feedstock is converted to an olefin-containing product while flowing through the reaction zone, the volumetric flow rate of the feedstock can vary throughout the reaction zone. In addition, depending upon reactor design, the cross-sectional area of the reaction zone may also vary at any given point within the reactor. Therefore, average GSV, as used herein, represents the average GSV throughout the reaction zone.

When the average GSV is greater than about 1 m/s, backmixing of gases in the reaction can be reduced, if not minimized. This increases the selectivity to the desired light olefins (e.g., ethylene and/or propylene), and also increases the approach to plug flow behavior of the gases flowing through the reaction zone. The velocity profile at a given cross section of the reaction zone under these conditions can be approximately flat and there can be little axial diffusion or backmixing of fluid elements. Ideal plug flow behavior occurs when elements of the homogeneous fluid reactant move through a reaction zone essentially as plugs moving parallel to the reactor axis.

In order to maintain plug flow behavior, as well as achieve relatively isothermal conditions within the reaction zone, it may be beneficial to recirculate a portion of the catalyst exiting the reaction zone to recontact the feed. This recirculation may occur either within the reaction zone or outside the reaction zone. Recirculating the catalyst can serve to decrease the temperature differential across the reaction zone (i.e., between the inlet and the outlet) by absorbing a portion of the heat generated by the exothermic conversion reaction. The outlet is the portion of the reaction zone at which the reactants (feed, catalyst system, and products) pass from the reaction zone to a catalyst disengaging zone. In one embodiment, the temperature differential across the reaction zone can be less than about 120° C., which is the practical limit of what could be considered near isothermal conditions in a continuously operating system. Preferably, the temperature differential is maintained at less than about 100° C., more preferably less than about 50° C. or less than about 30° C.

When catalyst is desirably recirculated to contact the feed, preferably, the rate of catalyst (including molecular sieve as well as any other materials present, such as binders, fillers, etc.) recirculated to contact the feed can be from about 1 to about 100 times the total feed rate of oxygenate fed to the reactor, more preferably from about 10 times to about 80 times or from about 10 times to about 50 times. In a process which includes a separate regenerator, at least a portion of the catalyst in the reactor can be desirably removed for regeneration and circulated back to the reactor at a rate from about 0.1 times to about 10 times the total feed rate of oxygenate to the reactor, preferably from about 0.2 times to about 5 times or from about 0.3 times to 3 times.

As also stated above, the at least partially regenerated catalyst can be used to manage heat within the conversion reactor. As one skilled in the art will appreciate, the conversion of the oxygenate feedstock to light olefins is an exothermic reaction. By returning the at least partially regenerated catalyst to contact the by-products of the conversion reaction, the longer-chain by-products of the conversion reaction can be converted (cracked) to shorter-chain olefin products, which are more desirable in some embodiments. The conversion of the longer-chain by-products to shorter-chain olefin products is an endothermic reaction. The conversion of the by-products into shorter-chain (preferably light) olefin products consumes heat produced by the conversion of the oxygenate feed, thus, reducing the overall heat of reaction in a reactor during a catalyzed chemical conversion process. By feeding the hot catalyst to the reactor, a catalyst cooler may be eliminated from the apparatus used to produce the desired olefins or, at least, the catalyst cooler can be reduced in size and/or cooling duty. The hot catalyst can be cooled in the reactor by the endothermic conversion of the longer-chain ($C_4$, $C_5$, $C_6$, and longer) olefins into ethylene, propylene, and coke.

The olefins produced by this invention can be easily separated, preferably as a result of the low amount of undesirable by-products produced, and the separated olefins can be manufactured into polyolefins, particularly ethylene- and/or propylene-containing polymers, such as polyethylene and polypropylene. The olefins produced according to this invention are preferably particularly high in ethylene and propylene content, generally with a high selectivity to ethylene. The desired olefin products include at least ethylene and propylene, and, in some cases, 1-butene may be a desired olefin product as well.

Processes for forming olefin-containing polymers (e.g. polyolefins) from olefins are known in the art. Though catalytic processes are preferred, non-catalytic processes are also contemplated. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

One preferred polyolefin-forming catalyst is a metallocene catalyst. A preferred temperature range of operation can be between 50° C. and 240° C., and the reaction can be carried out at low, medium, or high pressure, e.g., from about 1 bar to about 200 bar. For processes carried out in solution, an inert diluent can be used, and a preferred operating pressure range can be between about 10 bar and about 150 bar, with a preferred temperature range between about 120° C. and about 230° C. For gas phase processes, the temperature can generally be within a range from about 60° C. to about 160° C., and the operating pressure can be between about 5 bar and about 50 bar.

Additionally or alternately, the present invention can be described by the following embodiments.

Embodiment 1

A method for impregnating a molecular sieve primary catalyst with an aromatic co-catalyst, the method comprising: contacting the molecular sieve primary catalyst having a porous framework structure with a combination of from at least 50 wt % to about 99.9 wt % of an aromatic co-catalyst and from about 0.1 wt % to less than 50 wt % of a polar impregnation agent containing one or more heteroatoms selected from the group consisting of nitrogen, oxygen, sulfur, phosphorus, and boron, under conditions sufficient to impregnate the porous framework structure of the primary catalyst with the aromatic co-catalyst, thus forming an integrated catalyst system, wherein the molecular sieve primary catalyst (i) has an 8-membered ring porous framework structure, (ii) has a porous framework structure that is defined by a pore size not greater than 5.0 Angstroms and that exhibits an AEI framework type, a CHA framework type, or both, or (iii) has both (i) and (ii).

Embodiment 2

The method of embodiment 1, wherein one or more of the following are satisfied: (a) the combination contains from about 85 wt % to about 99.5 wt % of the aromatic co-catalyst and from about 0.5 wt % to about 15 wt % of the polar impregnation agent; (b) the aromatic co-catalyst is selected from the group consisting of benzene, toluene, xylene, ethylbenzene, methylethylbenzene, a $C_5$-$C_{14}$ linear, branched, or cyclic non-aromatic hydrocarbon having at least one unsaturation, and combinations thereof, (c) the polar impregnation agent is selected from the group consisting of water (vapor); ammonia; hydrogen sulfide; hydroxylamine; a $C_1$-$C_5$ alcohol, a $C_1$-$C_5$ diol, an amine compound $NR_3$, where each R group is independently hydrogen or a $C_1$-$C_5$ hydrocarbon; a hydroxy-amino-compound $R_2N$—R'—OH, where each R group is independently hydrogen or a $C_1$-$C_5$ hydrocarbon, and R' is a $C_1$-$C_5$ hydrocarbon; a thio-amino-compound $R_2N$—R'—SH, where each R group is independently hydrogen or a $C_1$-$C_5$ hydrocarbon, and R' is a $C_1$-$C_5$ hydrocarbon; a hydroxy-thio-compound RS—R'—OH, where each R group is independently hydrogen or a $C_1$-$C_5$ hydrocarbon, and R' is a $C_1$-$C_5$ hydrocarbon; a boron compound $BR_3$, where each R group is independently hydrogen or a $C_1$-$C_5$ hydrocarbon; mixtures thereof, and reaction products thereof, (d) the molecular sieve primary catalyst has both (i) and (ii) and comprises a silicoaluminophosphate, an aluminophosphate, or a metal-modified version thereof, and (e) the conditions sufficient to impregnate the porous framework structure of the primary catalyst with the aromatic co-catalyst comprise a temperature from about 200° C. to about 450° C., a pressure from about 250 psig to about 3000 psig, and an exposure time of at least about 3 minutes.

Embodiment 3

The method of embodiment 1 or embodiment 2, further comprising removing at least a portion of the polar impregnation agent from the porous framework structure by further thermally treating the integrated catalyst system at a treatment temperature from about 275° C. to about 550° C., but still higher than the temperature sufficient to impregnate the porous framework structure, for a treatment time of at least about 10 minutes.

Embodiment 4

The method of any of the previous embodiments, wherein the combination contains from about 10 wt % to about 99 wt % of the aromatic co-catalyst and from about 1 wt % to about 10 wt % of the polar impregnation agent.

Embodiment 5

The method of any of the previous embodiments, wherein the integrated catalyst system contains within its porous framework structure at least 85 wt % of the aromatic co-catalyst and not more than 15 wt % of the polar impregnation agent, based on thermally programmed oxidation analysis, carbon nuclear magnetic resonance analysis, or both.

Embodiment 6

The method of any of embodiments 2-5, wherein (a) and (e) are satisfied, wherein the aromatic co-catalyst comprises toluene and/or 2,3-dimethyl-2-butene, wherein the polar impregnation agent comprises methanol, ethanol, diisopropylethylamine, water, or ammonia, and wherein the molecular sieve is a silicoaluminophosphate molecular sieve having both AEI and CHA framework-type character.

Embodiment 7

A method for converting an oxygenate feedstock into an olefin-containing product, the method comprising: impregnating a molecular sieve primary catalyst with an aromatic co-catalyst according to the method of any of the previous embodiments to form an integrated catalyst system; contacting the oxygenate feedstock with the integrated catalyst system under conditions sufficient to form an olefin-containing product; and separating one or more olefins from the olefin-containing product.

Embodiment 8

The method of embodiment 7, wherein one or more of the following are satisfied: (a) the combination contains from about 85 wt % to about 99.5 wt % of the aromatic co-catalyst and from about 0.5 wt % to about 15 wt % of the polar impregnation agent; (b) the aromatic co-catalyst is selected from the group consisting of benzene, toluene, xylene, ethylbenzene, methylethylbenzene, a $C_5$-$C_{14}$ linear, branched, or cyclic non-aromatic hydrocarbon having at least one unsaturation, and combinations thereof, (c) the polar impregnation agent is selected from the group consisting of water (vapor); ammonia; hydrogen sulfide; hydroxylamine; a $C_1$-$C_5$ alcohol, a $C_1$-$C_5$ diol, an amine compound $NR_3$, where each R group is independently hydrogen or a $C_1$-$C_5$ hydrocarbon; a hydroxy-amino-compound $R_2N$—R'—OH, where each R group is independently hydrogen or a $C_1$-$C_5$ hydrocarbon, and R' is a $C_1$-$C_5$ hydrocarbon; a thio-amino-compound $R_2N$—R'—SH, where each R group is independently hydrogen or a $C_1$-$C_5$ hydrocarbon, and R' is a $C_1$-$C_5$ hydrocarbon; a hydroxy-thio-compound RS—R'—OH, where each R group is independently hydrogen or a $C_1$-$C_5$ hydrocarbon, and R' is a $C_1$-$C_5$ hydrocarbon; a boron compound $BR_3$, where each R group is independently hydrogen or a $C_1$-$C_5$ hydrocarbon; mixtures thereof, and reaction products thereof, (d) the molecular sieve primary catalyst has both (i) and (ii) and comprises a silicoaluminophosphate, an aluminophosphate, or a metal-modified version thereof, (e) the conditions sufficient to impregnate the porous framework structure of the primary catalyst with the aromatic co-catalyst comprise a temperature from about 200° C. to about 450° C., a pressure from about 250 psig to about 3000 psig, and an exposure time of at least about 3 minutes; and (f) the molecular sieve primary catalyst, when formulated by combining with a binder and optionally also a matrix, has an attrition resistance index of less than about 1 wt %/hr.

Embodiment 9

The method of embodiment 7 or embodiment 8, further comprising removing at least a portion of the polar impregnation agent from the porous framework structure by further thermally treating the integrated catalyst system at a treatment temperature from about 275° C. to about 550° C., but still higher than the temperature sufficient to impregnate the porous framework structure, for a treatment time of at least about 10 minutes.

Embodiment 10

The method of any of embodiments 7-9, wherein the integrated catalyst system contains within its porous framework structure at least 85 wt % of the aromatic co-catalyst and not more than 15 wt % of the polar impregnation agent, based on thermally programmed oxidation analysis, carbon nuclear magnetic resonance analysis, or both.

Embodiment 11

The method of any of embodiments 8-10, wherein (a), (e), and (f) are satisfied, wherein the aromatic co-catalyst comprises toluene and/or 2,3-dimethyl-2-butene, wherein the polar impregnation agent comprises methanol, ethanol, diisopropylethylamine, water, or ammonia, and wherein the molecular sieve is a silicoaluminophosphate molecular sieve having both AEI and CHA framework-type character.

Embodiment 12

An integrated catalyst system comprising a molecular sieve primary catalyst having a porous framework structure and an average pore diameter, within which is impregnated an aromatic co-catalyst having a kinetic diameter equal to or up to 2.0 Angstroms larger than the average pore diameter of the molecular sieve primary catalyst and optionally a polar impregnation agent containing one or more heteroatoms selected from the group consisting of nitrogen, oxygen, sulfur, phosphorus, and boron, wherein the molecular sieve primary catalyst (i) has an 8-membered ring porous framework structure, (ii) has a porous framework structure that is defined by a pore size not greater than 5.0 Angstroms and that exhibits an AEI framework type, a CHA framework type, or both, or (iii) has both (i) and (ii).

Embodiment 13

The integrated catalyst system of embodiment 12, wherein one or more of the following are satisfied: (a) the combination contains from about 85 wt % to about 99.9 wt % of the aromatic co-catalyst and from about 0.1 wt % to about 15 wt % of the polar impregnation agent; (b) the aromatic co-catalyst is selected from the group consisting of benzene, toluene, xylene, ethylbenzene, methylethylbenzene, a $C_5$-$C_{14}$ linear, branched, or cyclic non-aromatic hydrocarbon having at least one unsaturation, and combinations thereof, (c) the polar impregnation agent is selected from the group consisting of water (vapor); ammonia; hydrogen sulfide; hydroxylamine; a $C_1$-$C_5$ alcohol, a $C_1$-$C_5$ diol, an amine compound $NR_3$, where each R group is independently hydrogen or a $C_1$-$C_5$ hydrocarbon; a hydroxy-amino-compound $R_2N$—$R'$—$OH$, where each R group is independently hydrogen or a $C_1$-$C_5$ hydrocarbon, and R' is a $C_1$-$C_5$ hydrocarbon; a thio-amino-compound $R_2N$—$R'$—$SH$, where each R group is independently hydrogen or a $C_1$-$C_5$ hydrocarbon, and R' is a $C_1$-$C_5$ hydrocarbon; a hydroxy-thio-compound RS—R'—OH, where each R group is independently hydrogen or a $C_1$-$C_5$ hydrocarbon, and R' is a $C_1$-$C_5$ hydrocarbon; a boron compound $BR_3$, where each R group is independently hydrogen or a $C_1$-$C_5$ hydrocarbon; mixtures thereof, and reaction products thereof, and (d) the molecular sieve primary catalyst has both (i) and (ii) and comprises a silicoaluminophosphate, an aluminophosphate, or a metal-modified version thereof.

Embodiment 14

The integrated catalyst system of embodiment 12 or embodiment 13, wherein the combination contains from about 10 wt % to about 99 wt % of the aromatic co-catalyst and from about 1 wt % to about 10 wt % of the polar impregnation agent.

Embodiment 15

The integrated catalyst system of embodiment 13 or embodiment 14, wherein (a) is satisfied, wherein the aromatic co-catalyst comprises toluene and/or 2,3-dimethyl-2-butene, wherein the polar impregnation agent comprises methanol, ethanol, diisopropylethylamine, water, or ammonia, and wherein the molecular sieve is a silicoaluminophosphate molecular sieve having both AEI and CHA framework-type character.

EXAMPLES

Aspects of the present invention can be further described in the following examples, which are intended merely to illustrate the invention and not to limit its scope, as defined by the appended claims.

Example 1

Toluene is too large (roughly 5 Angstrom kinetic diameter) to fit through the 8-membered ring pore windows of SAPO-34 cages (roughly 3.8 Angstroms). Nevertheless, in Example 1, impregnation of toluene within SAPO-34 is accomplished by using a small amount of diisopropylethylamine.

About 5 grams of particles of a formulated SAPO-34 catalyst (containing about 45 wt % sieve and about 55 wt % binder) were loaded into a fixed bed, tubular reactor. The reactor was mounted into the furnace of a pilot unit equipped with a syringe pump and a back pressure regulator. The back pressure regulator was set to about 1000 psig. The reactor was heated to a variety of temperatures, including about 260° C., about 320° C., and about 380° C. When the reactor was hot, the syringe pump pushed a combination comprising about 99 wt % toluene and about 1 wt % diisopropylethylamine into the reactor at a flow rate of about 400 $cm^3$/hr for several minutes, until the unit reached about 1000 psig. Then, the flow rate was reduced to about 6 $cm^3$/hr. The reactor was held at these conditions for about 5 minutes, about 1 hour, or about 19 hours. After these times, the syringe pump was stopped, the furnace was shut off, and the unit was depressurized to about ambient atmospheric pressure. The catalyst was unloaded and analyzed using NMR and temperature programmed oxidation (TPO). The analytical results are shown in FIGS. 1 and 2.

TPO analyses involved milligram-scale samples being heated at relatively modest heating rates (e.g., between about 1° C./min and about 5° C./min). In addition to merely weight loss analysis from decomposition/combustion of the samples, TPO can be coupled with an analysis method allowing examination of the decomposed/combusted material being lost, e.g., gas chromatography, mass spectrometry, and the like.

Figure 1:
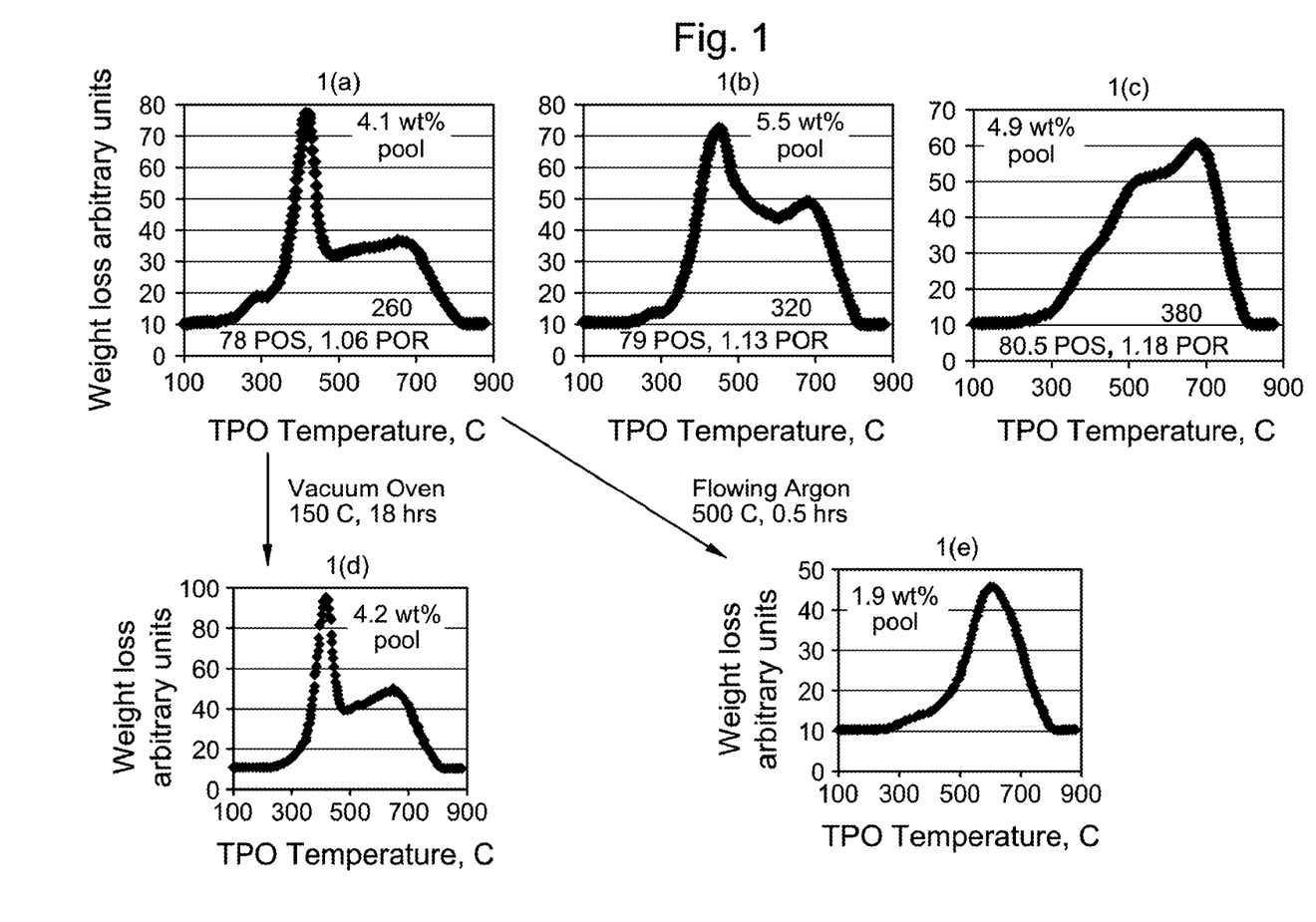
FIG. 1 shows a variety of temperature programmed oxidation curves for molecular sieve samples impregnated under various impregnation conditions in Example 1.
Figure 2:
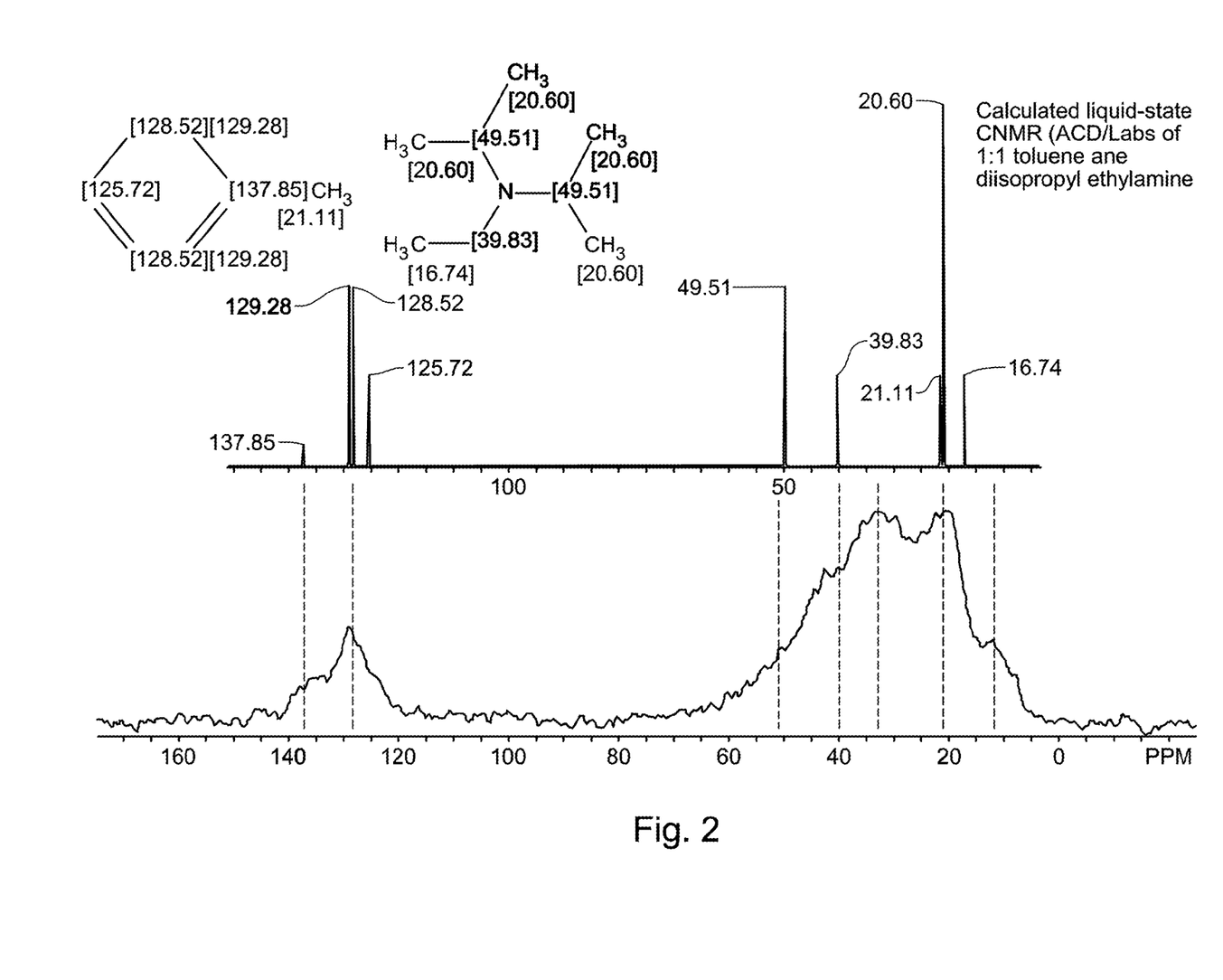
FIG. 2 shows a carbon nuclear magnetic resonance spectrum of one of the impregnated molecular sieve samples from Example 1.

FIG. 1(a), 1(b), and 1(c) show the result of impregnation at temperatures of about 260° C., about 320° C., and about 380°

C., respectively. FIG. 1(d) shows the results of heating the impregnated sample from FIG. 1(a) by heating in a vacuum oven (at a pressure less than 1 torr) to a temperature of about 150° C. for about 18 hours. Subsequent TPO indicated no measurable loss in the impregnated co-catalyst/impregnation agent combination within the porous framework structure of the molecular sieve under those conditions, which itself indicates stability. FIG. 1(e) shows the results of heating the impregnated sample from FIG. 1(a) by heating in a flowing argon atmosphere to a temperature of about 500° C. for about 30 minutes. Subsequent TPO indicated not only the significant disappearance of most (if not all) of the diisopropylethylamine but also the relative stability of the toluene within the porous framework structure of the molecular sieve under those conditions. For clarification, in the various TPO graphs in FIG. 1, weight loss between about 300° C. and about 500° C. is attributed to the degradation, combustion, and/or thermal decomposition of diisopropylethylamine, while weight loss between about 500° C. and about 800° C. is attributed to the degradation, combustion, and/or thermal decomposition of toluene. Confirmation of the presence of both toluene and diisopropylethylamine within the porous framework structure of the molecular sieve of FIG. 1(a) prior to TPO can be seen in the solid state 13C NMR spectrum of FIG. 2.

Example 2

In Example 2, like in Example 1, about 5 grams of particles of a formulated SAPO-34 catalyst (containing about 45 wt % sieve and about 55 wt % binder) were loaded into a fixed bed, tubular reactor. The reactor was mounted into the furnace of a pilot unit equipped with a syringe pump and a back pressure regulator. The back pressure regulator was set to about 1000 psig. The reactor was heated to a variety of temperatures, including about 380° C. and about 440° C. When the reactor was hot, the syringe pump pushed solely toluene (without any polar impregnation agent) into the reactor at a flow rate of about 400 cm$^3$/hr for several minutes, until the unit reached about 1000 psig. Then, the flow rate was reduced to about 6 cm$^3$/hr. The reactor was held at these conditions for about 19 hours. Thereafter, the syringe pump was stopped, the furnace was shut off, and the unit was depressurized to about ambient atmospheric pressure. The catalyst was unloaded and analyzed using TPO. The analytical results (not shown) indicate substantially no toluene impregnation under these conditions (while there was about a 0.2 wt % increase, such a small difference can be attributable to experimental measurement uncertainty), compared to the roughly 4-5.5 wt % loading in Example 1 at comparable conditions.

Examples 3-4 and Comparative Example 1

Comparative Example 1 represents a baseline of a formulated and calcined SAPO-34 catalyst (containing about 45 wt % sieve and about 55 wt % binder) that was not subject to impregnation. Example 3 uses the samples from Examples 1(a), 1(b), and 1(c), with the impregnation time of about 19 hours. Example 4 uses the samples from Example 1(a) with the impregnation times of about 5 minutes, about 1 hour, and about 19 hours.

Figure 3:
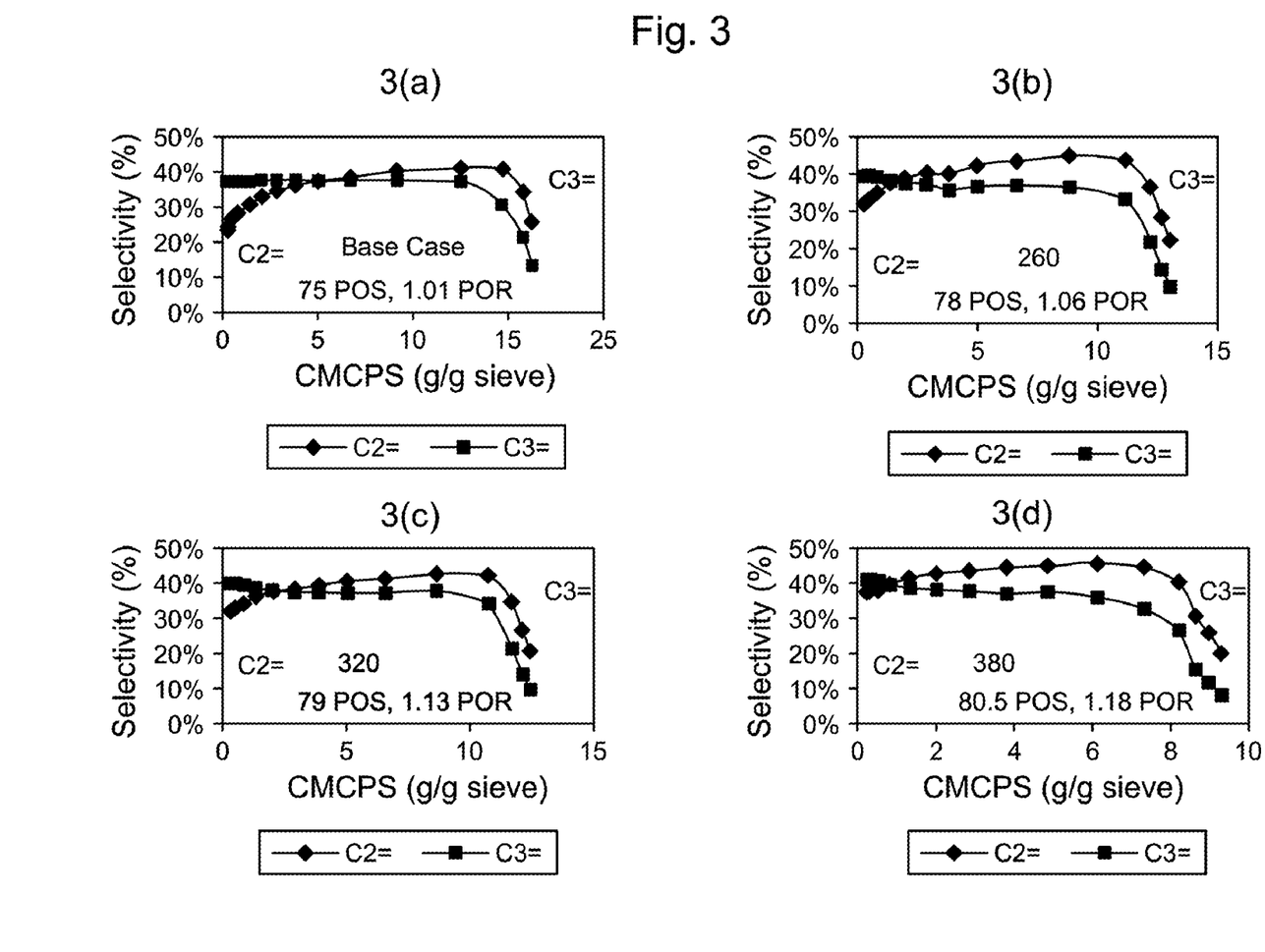
FIG. 3 shows a variety of graphs of olefin selectivity versus catalyst life, expressed as content of methanol converted per content of sieve, for products of MTO reactions using an unimpregnated molecular sieve sample (Comparative Example 1) and various impregnated molecular sieve samples (from Example 1).
Figure 4:
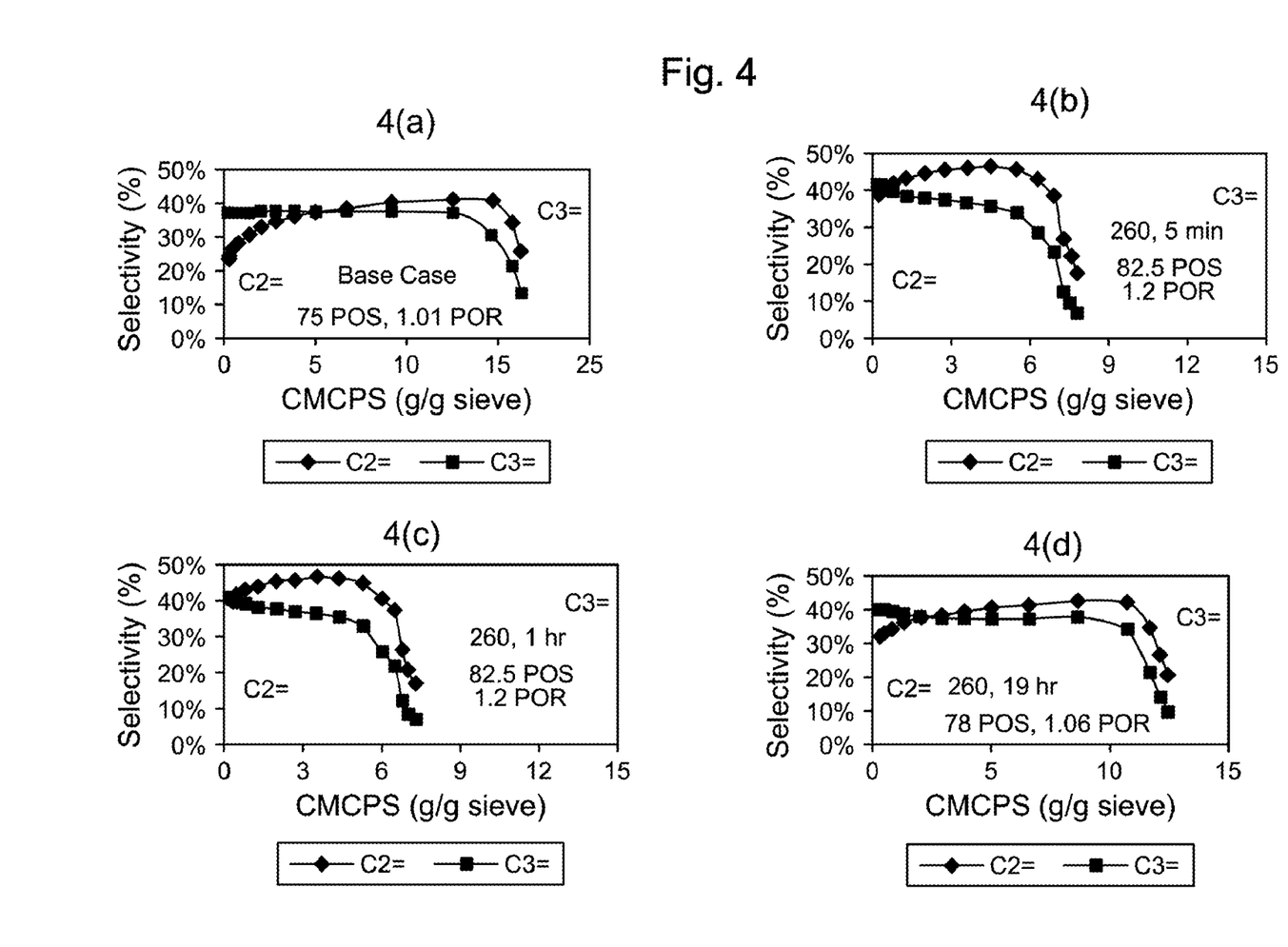
FIG. 4 shows a variety of graphs of olefin selectivity versus catalyst life, expressed as content of methanol converted per content of sieve, for products of MTO reactions using an unimpregnated molecular sieve sample (Comparative Example 1) and an impregnated molecular sieve sample from Example 1 under various impregnation conditions.

All the catalyst samples of Examples 3-4 and Comparative Example 1 were used to convert methanol to olefins at the following reaction conditions: WHSV of about 100 hr$^{-1}$, about 25 psig reactor pressure, and about 500° C. average reactor temperature. FIG. 3 shows the effect of impregnation temperature on ethylene and propylene selectivity for these MTO reactions as a function of the content of methanol converted per content of molecular sieve (CMCPS, expressed in grams oxygenate converted per gram of molecular sieve, not including the weight of any binder and/or matrix material, until the reaction proceeds to about 10% conversion or below). FIG. 3(a) represents the "base case" of Comparative Example 1, while FIGS. 3(b), 3(c), and 3(d) represent Examples 1(a), 1(b), and 1(c) (i.e., with impregnation temperatures of about 260° C., about 320° C., and about 380° C., respectively), with the impregnation time of about 19 hours. FIG. 4 shows the effect of impregnation time on ethylene and propylene selectivity for these MTO reactions as a function of CMCPS. FIG. 4(a) again represents the "base case" of Comparative Example 1, while FIGS. 4(b), 4(c), and 4(d) represent Example 1(a) (i.e., with an impregnation temperature of about 260° C.) with impregnation times of about 5 minutes, about 1 hour, and about 19 hours, respectively.

Example 5

About 5 grams of particles of a formulated SAPO-34 catalyst (containing about 45 wt % sieve and about 55 wt % binder) were loaded into a fixed bed, tubular reactor. The reactor was mounted into the furnace of a pilot unit equipped with a syringe pump and a back pressure regulator. The back pressure regulator was set to about 1000 psig. The reactor was heated to about 260° C. When the reactor was hot, the syringe pump pushed a combination comprising about 90 wt % toluene and about 10 wt % methanol into the reactor at a flow rate of about 400 cm$^3$/hr for several minutes, until the unit reached about 1000 psig. Then, the flow rate was reduced to about 6 cm$^3$/hr. The reactor was held at these conditions for about 1 hour or about 19 hours. After these times, the syringe pump was stopped, the furnace was shut off, and the unit was depressurized to about ambient atmospheric pressure.

Figure 5:
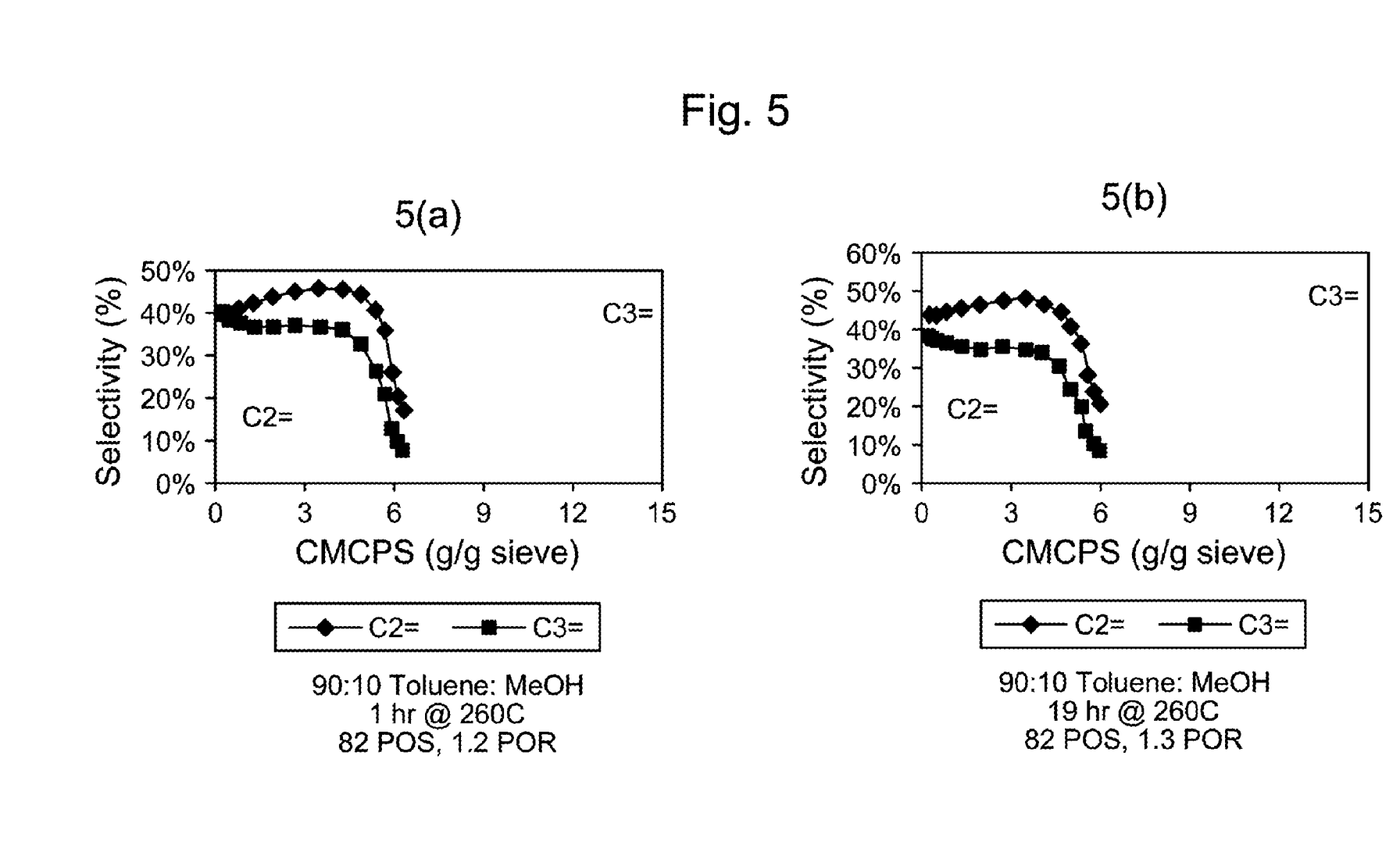
FIG. 5 shows the effect of impregnation time in several graphs of olefin selectivity versus catalyst life, expressed as content of methanol converted per content of sieve, for products of MTO reactions using an impregnated molecular sieve sample from Example 1 subject to two different impregnation times.

The impregnated catalyst samples of Example 5 were used to convert methanol to olefins at the following reaction conditions: WHSV of about 100 hr$^{-1}$, about 25 psig reactor pressure, and about 500° C. average reactor temperature. FIG. 5 shows the effect of impregnation time on ethylene and propylene selectivity for these MTO reactions as a function of CMCPS. FIG. 5(a) represents the results from an integrated catalyst system having an impregnation temperature of about 260° C. with an impregnation time of about 1 hour, while FIG. 5(b) represents the results from an integrated catalyst system having an impregnation temperature of about 260° C. with an impregnation time of about 19 hours. These results can be compared with Examples 4(c) and 4(d), respectively, to ascertain the relative differences between combination compositions.

It is noted that the methanol impregnation agent does not seem to displace the toluene co-catalyst at relatively longer impregnation times, which is in contrast with the results from the diisopropylethylamine impregnation agent, even when the latter was present at a much lower concentration.

Examples 1 and 3-5, in contrast to Example 2 and the Comparative Example, also indicated a relatively high level of combination composition (co-catalyst) impregnation, amounting to at least about 80% and up to about 100% of the cages having been filled in the porous framework structure of the molecular sieve primary catalyst under the experimental impregnation conditions.

Further, in the Example shown in FIG. 4(b), the catalyst exhibited an average ethylene selectivity of about 44.2%, compared to an average ethylene selectivity of about 37.9% for the catalyst of Comparative Example 1. This means the catalyst impregnated with toluene has a more than 15% higher selectivity to ethylene than a non-impregnated catalyst. According to further analyses, the increased ethylene is apparently produced entirely at the expense of relatively low value products—$C_{4+}$ olefins, coke, and $C_{3-}$ paraffins.

The Examples also show that the integrated catalyst systems according to the invention have a relatively shorter lifetime that similar non-impregnated molecular sieve catalyst compositions (compare Comparative Example 1). It is believed that the catalyst lifetime (as measured by CMCPS) can be improved/optimized, when operated under the pulse conditions characteristic of a fast fluid bed reactor.

It should be appreciated by one of ordinary skill in the art that any embodiments, though listed separately, may additionally or alternately be combined together to form compositions, articles, and/or methods according to the invention, to the extent that such combinations are not expressly mutually exclusive. In addition, it should be understood by one of ordinary skill in the art that the embodiments according to the invention may be altered through undue experimentation without departing from the scope of the present invention. For instance, though relatively small pore molecular sieve primary catalysts and relatively small kinetic diameter "bulky" unsaturated and aromatic co-catalysts are disclosed hereinabove with reference to oxygenate-based hydrocarbon conversion reactions, it is believed that the impregnation methods of the invention should be applicable, without undue experimentation, to relatively larger pore molecular sieve catalysts and relatively larger kinetic diameter co-catalysts with reference to other non-oxygenate-based carbon-assembling reactions.

All documents described herein are incorporated by reference herein, including any priority documents and/or testing procedures to the extent they are not inconsistent with this text. As is apparent from the foregoing general description and the specific embodiments, while forms of the present invention have been illustrated and described, various modifications can be made without departing from the spirit and scope of the invention. Accordingly, it is not intended that the invention be limited thereby.

What is claimed is:

1. A method for impregnating a molecular sieve primary catalyst with an aromatic co-catalyst, the method comprising:
    contacting the molecular sieve primary catalyst having a porous framework structure with a combination of from at least 50 wt % to about 99.9 wt % of an aromatic co-catalyst and from about 0.1 wt % to less than 50 wt % of a polar impregnation agent containing one or more heteroatoms selected from the group consisting of nitrogen, oxygen, sulfur, phosphorus, and boron, under conditions sufficient to impregnate the porous framework structure of the primary catalyst with the aromatic co-catalyst, thus forming an integrated catalyst system;
    removing at least a portion of the polar impregnation agent from the porous framework structure by further thermally treating the integrated catalyst system at a treatment temperature from about 275° C. to about 500° C., but higher than the temperature sufficient to impregnate the porous framework structure, for a treatment time of at least about 10 minutes;
    wherein the molecular sieve primary catalyst (i) has an 8-membered ring porous framework structure, (ii) has a porous framework structure that is defined by a pore size not greater than 5.0 Angstroms and that exhibits an AEI framework type, a CHA framework type, or both, or (iii) has both (i) and (ii); and
    wherein the integrated catalyst system contains within its porous framework structure at least 85 wt % of the aromatic co-catalyst and not more than 15 wt % of the polar impregnation agent, based on thermally programmed oxidation analysis, carbon nuclear magnetic resonance analysis, or both.

2. The method of claim 1, wherein one or more of the following are satisfied:
    (a) the combination contains from about 85 wt % to about 99.5 wt % of the aromatic co-catalyst and from about 0.5 wt % to about 15 wt % of the polar impregnation agent;
    (b) the aromatic co-catalyst is selected from the group consisting of benzene, toluene, xylene, ethylbenzene, methylethylbenzene, and combinations thereof;
    (c) the polar impregnation agent is selected from the group consisting of water (vapor); ammonia; hydrogen sulfide; hydroxylamine; a $C_1$-$C_5$ alcohol, a $C_1$-$C_5$ diol, an amine compound $NR_3$, where each R group is independently hydrogen or a $C_1$-$C_5$ hydrocarbon; a hydroxy-amino-compound $R_2N$—R'—OH, where each R group is independently hydrogen or a $C_1$-$C_5$ hydrocarbon, and R' is a $C_1$-$C_5$ hydrocarbon; a thio-amino-compound $R_2N$—R'—SH, where each R group is independently hydrogen or a $C_1$-$C_5$ hydrocarbon, and R' is a $C_1$-$C_5$ hydrocarbon; a hydroxy-thio-compound RS—R'—OH, where each R group is independently hydrogen or a $C_1$-$C_5$ hydrocarbon, and R' is a $C_1$-$C_5$ hydrocarbon; a boron compound $BR_3$, where each R group is independently hydrogen or a $C_1$-$C_5$ hydrocarbon; mixtures thereof; and reaction products thereof;
    (d) the molecular sieve primary catalyst has both (i) and (ii) and comprises a silicoaluminophosphate, an aluminophosphate, or a metal-modified version thereof; and
    (e) the conditions sufficient to impregnate the porous framework structure of the primary catalyst with the aromatic co-catalyst comprise a temperature from about 200° C. to about 450° C., a pressure from about 250 psig to about 3000 psig, and an exposure time of at least about 3 minutes.

3. The method of claim 2, wherein (a) and (e) are satisfied, wherein the aromatic co-catalyst comprises toluene and/or 2,3-dimethyl-2 butene, wherein the polar impregnation agent comprises methanol, ethanol, diisopropylethylamine, water, or ammonia, and wherein the molecular sieve is a silicoaluminophosphate molecular sieve having both AEI and CHA framework-type character.

4. The method of claim 1, wherein the removal step takes place in an inert gas atmosphere.

* * * * *